United States Patent [19]

Baxter, Jr.

[11] Patent Number: 5,532,679
[45] Date of Patent: Jul. 2, 1996

[54] OIL SPILL DETECTION SYSTEM

[76] Inventor: John F. Baxter, Jr., 930 Heron Ct., Marco Island, Fla. 33937

[21] Appl. No.: 391,424

[22] Filed: Feb. 16, 1995

Related U.S. Application Data

[63] Continuation of Ser. No. 124,347, Sep. 20, 1993, abandoned, which is a continuation of Ser. No. 102,271, Aug. 5, 1993, abandoned.

[51] Int. Cl.$^6$ .............................. G08B 1/08; E02B 15/04
[52] U.S. Cl. .......................... 340/539; 340/601; 340/623; 340/693; 73/440; 73/170.22; 73/170.34; 73/314; 405/66; 405/69; 210/923; 210/242.3
[58] Field of Search .................................... 340/539, 531, 340/601, 627, 623, 693; 73/32 R, 437, 440, 451, 53.01, 170.22, 170.29, 170.34, 305–312, 314; 405/66, 68, 69; 210/922, 923, 242.3

[56] References Cited

U.S. PATENT DOCUMENTS 3,603,952  9/1971  Smith ....................................... 340/539
3,719,936  3/1973  Daniels et al. .......................... 340/539
3,918,034  11/1975  Orth, Jr. ................................. 340/539
4,058,802  11/1977  Meyers ................................... 340/539

Primary Examiner—Donnie L. Crosland
Attorney, Agent, or Firm—A. W. Fisher, III

[57] ABSTRACT

An oil spill detection system to detect and track oil spills and transmit data to a remote monitoring center comprising a buoyant detection platform including at least one detection sensor to detect the presence of hydrocarbons in the water adjacent the buoyant detection platform and generate a detection signal in response thereto and a communication system operatively coupled to the detection sensor to receive the detection signal and to generate a data signal in response to the detection signal and to transmit the data signal to the remote monitoring center, the data signal including a discrete platform identification signal corresponding to the buoyant detection platform, and a deployable free floating tracking buoy to be deployed when the detection signal is generated to indicate the direction and speed of travel of the oil slick created by the oil spill.

11 Claims, 5 Drawing Sheets

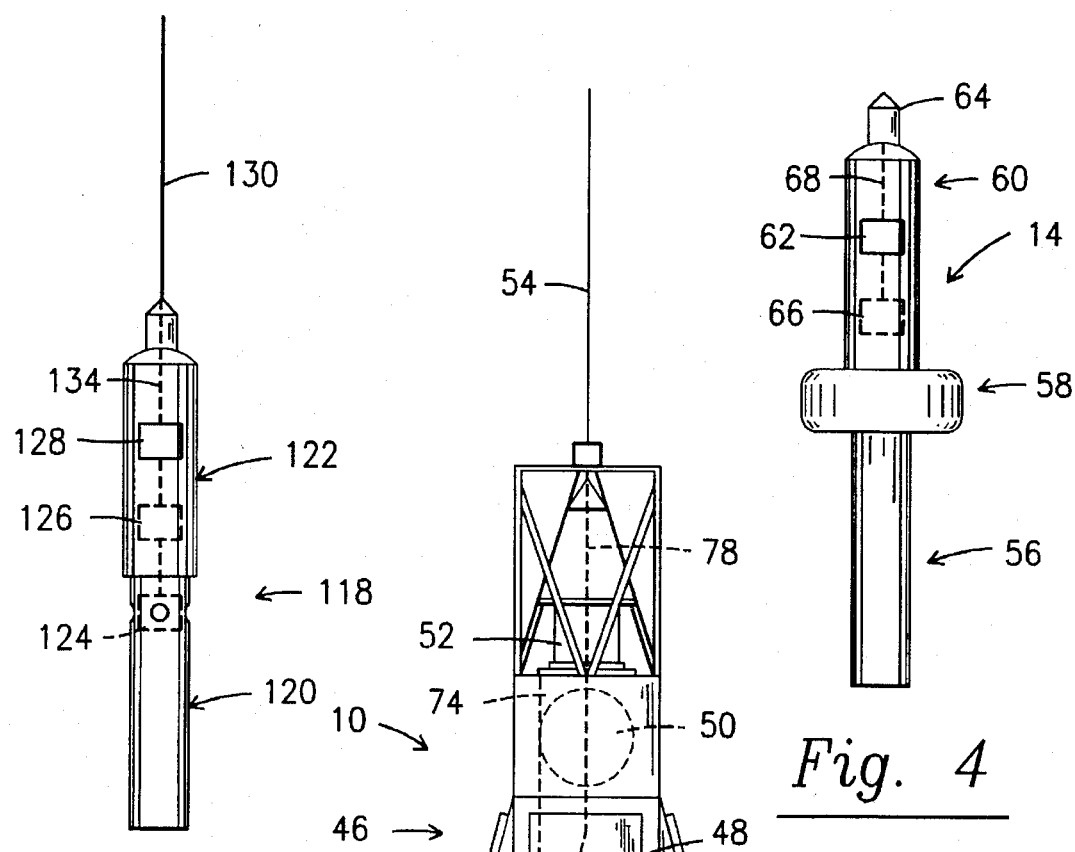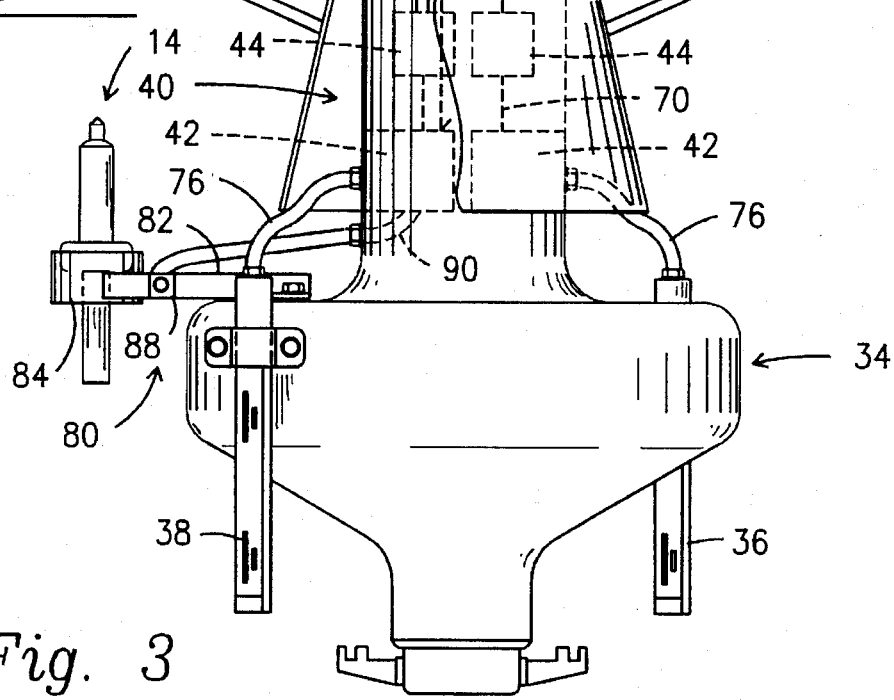

OIL SPILL DETECTION SYSTEM

CROSS REFERENCE

This application is a continuation application of pending application Ser. No. 08/124,347, filed Sep. 20, 1993, abandoned, which is a continuation of application Ser. No. 08/102,271, filed Aug. 5, 1993, abandoned.

BACKGROUND OF THE INVENTION

1. Field of the Invention

An oil spill detection system to detect and locate oil spillage in a body of water.

2. Description of the Prior Art

Oil spills, large and small, are among today's most environmentally damaging events. Even relatively small spills that normally go undetected can wreck havoc with the ecosystem. Early detection is vital in containing and cleaning up oil spills before such spills reach populated areas, protected coastal environments and inland waterways.

U.S. Pat. No. 3,719,936 discloses a system for the detection of oil spillage in water including a housing adapted to be disposed in a partially submerged buoyant state in a body of water and having a plurality of ports to allow entry of water and oil that is present on the surface thereof. A selectively transmissive permeable membrane of the hydrophobic hypophylic type is disposed within the housing in liquid communication with the oil-water interface. Only oil is transmitted through the permeable membrane to a chamber within the housing having a sensor disposed therein to detect the presence of oil and to generate an output signal of the oil when detected. The sensor comprises a resistance temperature dependent electrical thermometer or mechanically actuable by the weight of oil within the chamber to generate the output signal. The chamber can be removed from the detection system to permit collection of oil samples for analysis to determine the nature and source of the contaminant. In addition, a plurality of chambers can be provided to permit the sequential collection of a corresponding plurality of oil samples over time. A marking material can also be released to visually mark the spill site.

SUMMARY OF THE INVENTION

The present invention relates to an oil spill detection system to detect the presence of oil in harbors, bays, gulfs, canals, rivers, environmentally sensitive coastal waters, recreational beach areas, heavily traveled shipping lanes, lakes and waters.

The oil spill detection system comprises a buoyant detection platform and deployable free floating tracking buoy for use in combination with a remote monitoring or control system. More specifically, the buoyant detection platform comprises a sensor means and communication system to detect the presence of oil and transmit data to the remote monitoring system.

The sensing means comprises two electronic hydrocarbon sensing devices extending downwardly from the buoyant detecting platform into the water. When one of the sensing devices detects the presence of hydrocarbon, a first detection signal is generated and transmitted to the communication system and held for a predetermined time period such as ten seconds until the second sensing device also detects the presence of the hydrocarbon and generates a second detection signal which is also transmitted to the communication system. The communication system includes means to generate a data signal in response to the two detection signals and to transmit the data signal to the remote monitoring system to warn of the oil spill. The two sensing devices can be calibrated to detect different densities of oil or hydrocarbon spills.

In use, the buoyant detection platform is anchored or tethered in the body of water to be monitored for oil spillage. In operation, when hydrocarbons are detected by the sensing means, the communication system transmits the data signal to the remote monitoring system and/or other remote site such as a predetermined telephone or alternate remote receiving device. Each buoyant detection platform has a unique or discrete identifiable signal to identify the origin of the data signals.

Time and date data of the detected oil spill are recorded on the buoyant detection platform. In turn, the data signal including date, time and identification of the buoyant detection platform are transmitted to the remote monitoring center.

Once an oil spill has been detected, the free floating tracking buoy is deployed into the spill area to monitor the direction and speed of travel of the oil slick created by the oil spill.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which:

FIG. 3 is a detailed view of the buoyant detection platform of the present invention.

FIG. 4 is a detailed view of the deployable free floating tracking buoy of the present invention.

FIG. 6 is a partial detailed view of an alternate embodiment of the deployable free floating tracking buoy of the present invention.

Similar reference characters refer to similar parts throughout the several views of the drawings.

DETAILED DESCRIPTION OF THE PREFERRED EMBODIMENT

The present invention relates to an oil spill detection system to detect the presence of oil in harbors, bays, gulfs, canals, rivers, environmentally sensitive coastal waters, recreational beach areas, heavily traveled shipping lanes, lakes and waters.

Figure 1:
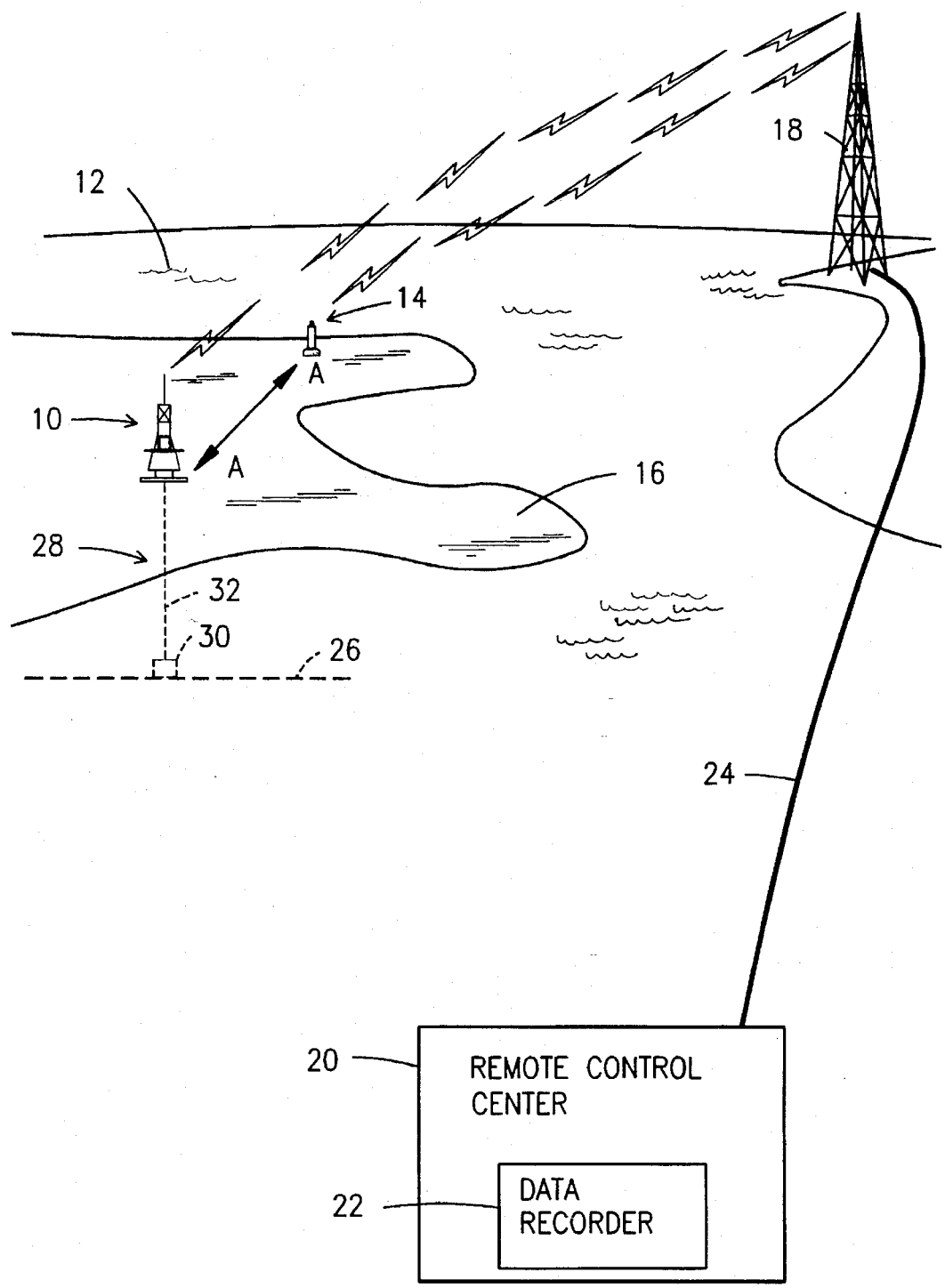
FIG. 1 shows the oil spill detection system of the present invention deployed in a body of water.

As best shown in FIG. 1, the oil spill detection system comprises a stationary buoyant detection platform generally indicated as 10 deployed in the body of water 12 to be monitored for use with a remote monitoring system comprising a communication tower 18 and a remote control center 20 including data recorder 22 operatively coupled by a communication cable or link 24 and a deployable free floating tracking buoy 14 to be deployed when an oil slick 16 is detected. Alternately, the data recorder 22 may be located externally of the remote control center 20 to receive data directly from the communication tower 18 or the buoyant detection platform 10. When deployed, the buoyant detection platform 10 is tethered or anchored to the bottom 26 of the body of water 12 by an anchor system generally indicated as 28 including an anchor 30 and flexible interconnecting member 32.

As best shown in FIG. 3, the stationary buoyant detection platform 10 comprises a lower floatation chamber generally indicated as 34 having a sensing means including a first detection sensor 36 and second detection sensor 38 attached thereto, an intermediate housing generally indicated as 40 to operatively house a communication means including one or more communication modules 42 and a power source including a plurality of storage batteries each indicated as 44, and an upper support structure generally indicated as 46 to operatively support a plurality of solar cells each indicated as 48, a radar reflector 50, a marine lantern or beacon 52 and a communication antenna 54.

The first and second detection sensors 36 and 38 each comprises a state of the art fluorometer including an automatic temperature composition means capable of detecting and measuring hydrocarbons in petroleum and petroleum by-products in the parts-per-billion range when present in the water 12 adjacent the buoyant detection platform 10. The first and second detection sensors 36 and 38 include means to generate a detection signal when the hydrocarbons are sensed.

The communication system includes means to receive the detection signals from the first and second detection sensors 36 and 38 and to generate a data signal in response thereto for transmission to the remote monitoring or control site as described more fully hereinafter. The communication system may also include a receiver for two-way communication.

As best shown in FIG. 4, the free floating tracking buoy 14 comprises a lover ballast generally indicated as 56, an intermediate float chamber generally indicated as 58 and an upper support housing generally indicated as 60 to operatively support a radar reflector 62 and a beacon 64 and to operatively house a power source such as a storage battery 66 electrically connected to the beacon 64 by a conductor 68 to selectively power the beacon 64 when the free floating tracking buoy 14 is deployed. Of course, a transmitter/receiver combination may be included to provide communication between the free floating tracking buoy 14 and a remote site.

As shown in FIG. 3, the storage batteries 44 are coupled to the communication system comprising one or more communication modules 42 by conductors 70, to the solar cells 48 by conductors 72 and the marine lantern or beacon 52 by conductor 74. The communication system or communication module 42 are coupled to the first and second detection sensors 36 and 38 by cables 76 and to the communication antenna 54 by a conductor or cable 78.

Figure 5:
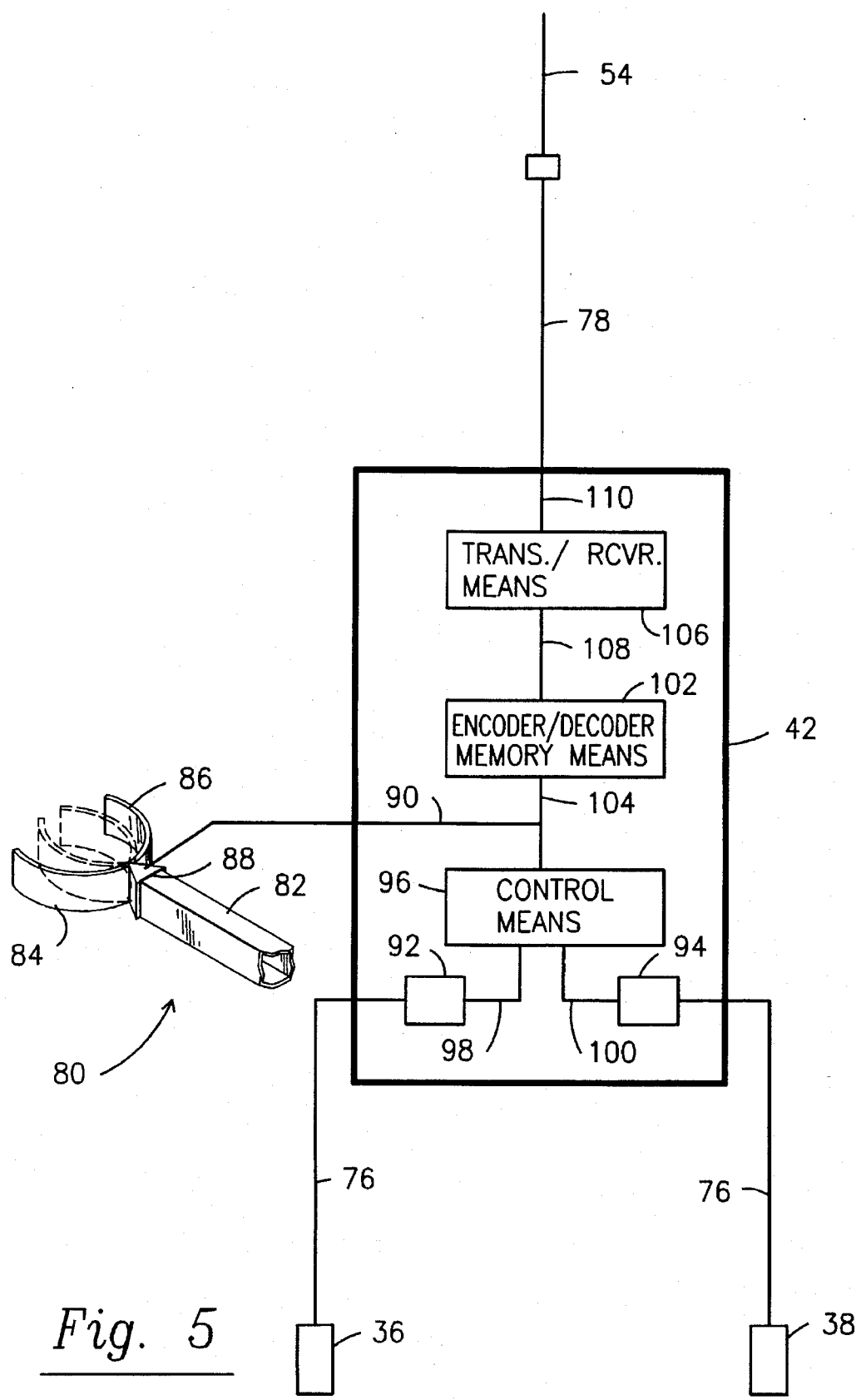
FIG. 5 is a schematic diagram of the communication system of the present invention.

As shown in FIGS. 3 and 5, a tracking buoy retainer device generally indicated as 80 is affixed to the side of the lower floatation buoy 34 to selectively retain the free floating tracking buoy 14. The tracking buoy retainer device 80 comprises an offset member 82 having a clamp including a first and second clamp element indicted as 84 and 86 respectively movable between an open and closed position and an actuator 88 such as a solenoid coupled to the communication module 42 by a conductor 90.

The communication system can best be understood by reference to FIG. 5. Specifically, the communication system or communication module 42 comprises a first and second latch or switch indicated as 92 and 94 respectively operatively coupled to the first and second detection sensors 36 and 38 respectively by the corresponding cable 76. The first latch or switch 92 including a time delay device and the second latch or switch 94 are operatively coupled to a control means 96 such as a latch or switch including circuitry to generate a control signal by conductors 98 and 100 respectively, when the detection sensors 36 and 38 detect the presence of hydrocarbon, a first detection signal is generated and transmitted to the communication system and held for a predetermined time period such as ten seconds until the second detection sensor 36 or 38 also detects the presence of the hydrocarbons and generates a second detection signal which is also transmitted to the communication system. The control means 96 then generates an enable signal in response to the two detection signals. The output of the control means 96 is operatively coupled to the tracking buoy retainer device 80 and an encoder/decoder/memory means 102 by a conductor 104 to transmit the control signal thereto. The encoder/decoder/memory means 102 includes circuitry to generate a data signal in response to the control signal transmitted to a transmitter/receiver means 106 through conductor 108 that is, in turn, fed to the communication antenna 54 through conductor 110 for transmission to the remote monitoring system to warn of an oil spill. The encoder/decoder memory means 102 also includes a memory medium to record operation of the communication system or communication module 42. Further, the transmitter/receiver 106 permits polling or interrogation of the operation and status of the oil spill detection system from a remote site.

In use, the stationary buoyant detection platform 10 is anchored or tethered in the body of water 12 to monitor for oil spills. In operation, when hydrocarbons are detected by the sensing means, the communication system transmits the data signal to the remote monitoring system and/or other remote site such as a predetermined telephone or alternate remote receiving device. Each buoyant detection platform 12 has a unique or discrete identification signal to identify the origin of the data signal to indicate the specific location of an oil spill when an array of such buoyant detection platforms 10 are deployed.

Time and date data of the detected oil spill are recorded on the buoyant detection platform 10. In turn, the data including date and time and identification of the transmitting buoyant detection platform are transmitted to the remote monitoring center.

Once an oil spill has been detected, the free floating tracking buoy 14 is deployed into the oil spill by moving the first and second clamp elements 84 and 86 from the closed to open position by activation of the actuator 88. The position of the deployable free floating tracking buoy 14 may be determined from the radar reflector 62 or the beacon 64 or through a transmitter. Since the location of the stationary buoyant detection platform 10 is known and since the deployable free floating tracking buoy 14 floats freely along with the oil slick created by the oil spill the location of the deployable free floating tracking buoy 14 relative to the stationary buoyant detection platform 10 indicated the direction and speed of travel of the oil slick as shown in FIG. 1.

Figure 2:
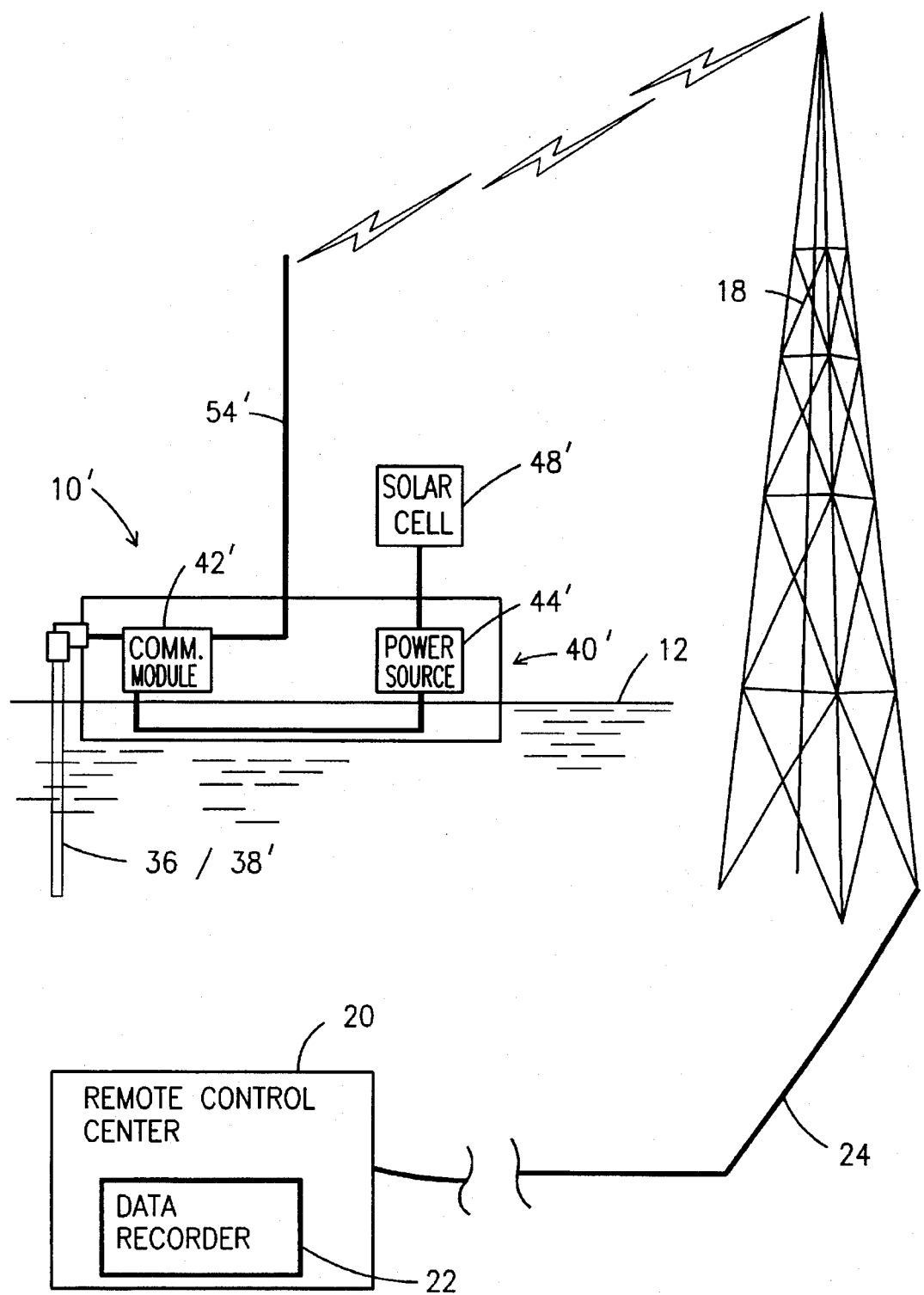
FIG. 2 shows an alternate embodiment of the oil spill detection system of the present invention deployed in a body of water.

FIG. 2 shows an alternate embodiment of the buoyant detection platform 10 comprising a sensing means including a first and second detection sensor 36'/38', housing generally indicated as 40' to operatively house a communication means including a plurality of communication modules each indicated as 42' and a power source 44' to operatively support a solar cell 48' and a communication antenna 54. The function and operation of this alternate embodiment is similar to that of the preferred embodiment.

Figure 7:
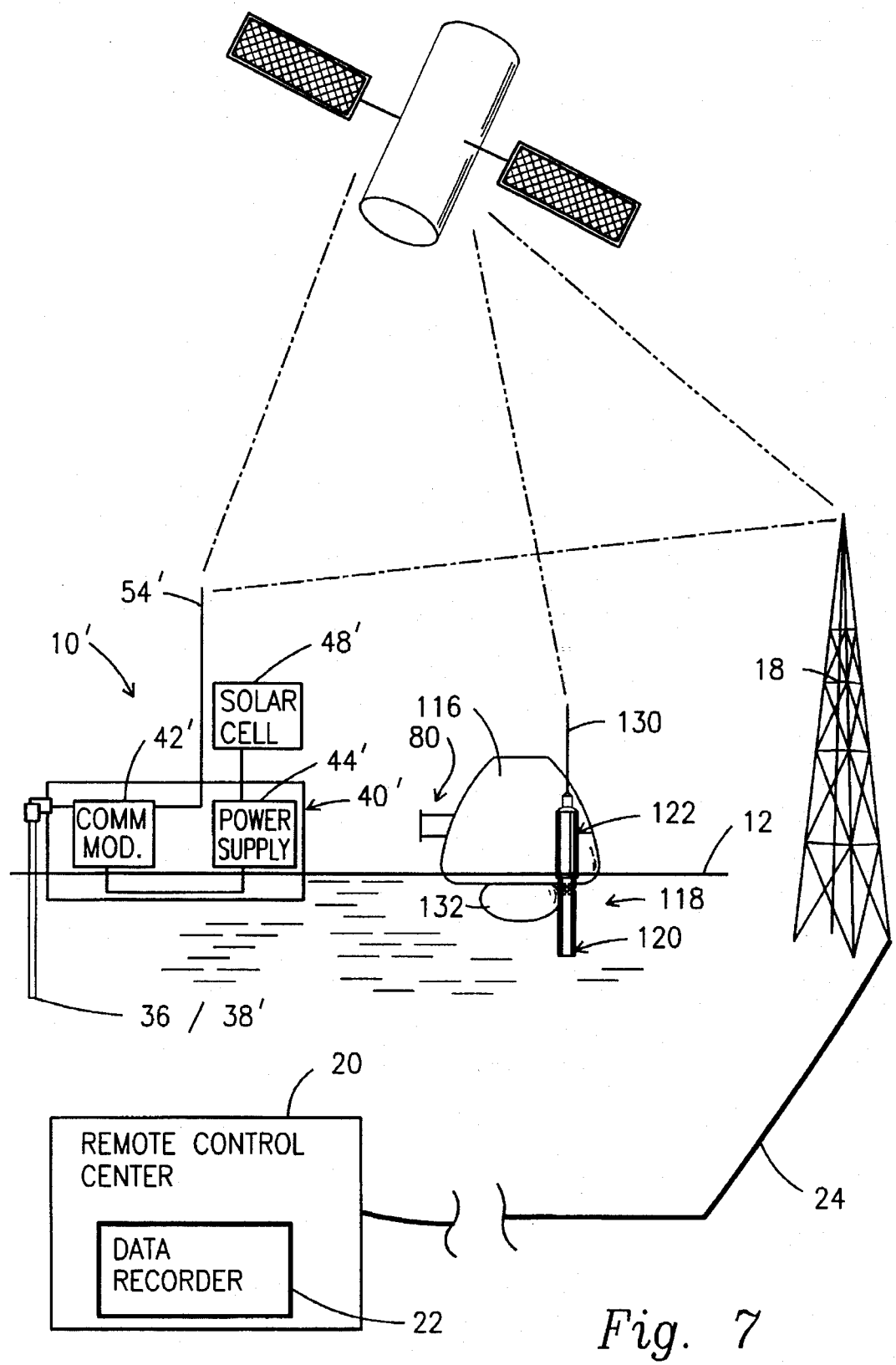
FIG. 7 shows the alternate embodiment of the deployable free floating tracking buoy of FIG. 6 deployed from the oil spill detection system of FIG. 2 employing satellite communications.

FIGS. 6 and 7 show an alternate embodiment of a free floating tracking buoy generally indicated as 112 for use with either of the buoy detection platforms 10 or 101 and transmission of data either directly to the communication tower 18 or through a satellite station 114.

As shown in FIGS. 6 and 7, the free floating tracking buoy 112 comprises a bulbous floatation member 116 having a sensing means generally indicated as 118 attached to the side thereof including a lower detection sensor 120 and an upper housing 122 to operatively house a communication means including at least one communication module 124 and a power source including at least one storage battery 126 to operatively support at least one solar cell 128 and a communication antenna 130. A ballast 132 attached to the bottom of the bulbous floatation member 116.

The lower detection sensor 120 comprises a state of the art fluorometer including an automatic temperature composition means capable of detecting and measuring hydrocarbons in petroleum and petroleum by-products in the parts-per-billion range when present in the water 12 adjacent the buoyant detection platform 10 or 101. The lower detection sensor 120 includes means to generate a detection signal when the hydrocarbons are sensed.

The communication system includes means to receive the detection signals from the lower detection sensor 120 and to generate a data signal in response thereto for transmission to the remote monitoring or control site as described with reference to the communication system of FIGS. 3 and 5.

As shown in FIG. 6, the storage battery 126 is coupled to the communication module 124 and to the solar cell 128 by a cable 134. The communication system or communication module 124 is also coupled to the lower detection sensor 120 and to the communication antenna 130 by the cable 134. The communication system of this alternate embodiment is similar to that described with reference to FIGS. 3 and 5.

Although the sensing means in intended for use to detect hydrocarbons, alternate sensors may be employed to detect other contaminates. The oil spill detection system can also be effectively used with existing floating bell buoys and light buoys; rigid navigational aids; peninsulas or islands; offshore platforms; jetties and breakwaters; docks and piers; canal locks and rivers.

Now that the invention has been described,
What is claimed is:

1. An oil spill detection system to detect and track oil spills and transmit data to a remote monitoring site comprising a stationary buoyant detection platform including a sensing means to detect the presence of hydrocarbons in the water adjacent said stationary buoyant detection platform and to generate a detection signal in response thereto and a communication means operatively coupled to said sensing means to receive said detection signal and to generate a data signal in response to said detection signal and to transmit said data signal to the remote monitoring site, and a deployable free floating tracking buoy detachably attached to said stationary buoyant detection platform by a tracking buoy retainer device movable between an open position to release said deployable free floating tracking buoy and a closed position to retain said deployable free floating tracking buoy, said tracking buoy retainer device operatively coupled to said communications means and further including control means to generate an enable signal in response to said detection signal and to transmit said enable signal to said tracking buoy retainer device to move said tracking buoy retainer device from said closed position to said open position to release said deployable free floating tracking buoy from said stationary buoyant detection platform into the oil such that said deployable free floating tracking buoy floats with the oil slick created by the oil spill whereby the location of said deployable free floating tracking buoy relative to said stationary buoyant detection platform indicates the direction and speed of travel of the oil slick.

2. The oil spill detection system of claim 1 wherein said buoyant detection platform comprises a lower floatation chamber to support said sensing means, an intermediate housing to operatively house said communication means and a power source and an upper support structure to operatively support said power source and a communication antenna.

3. The oil spill detection system of claim 1 wherein said sensing means includes a first detection sensor and a second sensor, when said detection sensors detect the presence of hydrocarbons, a first detection signal is generated and transmitted to said communication means and held for a predetermined time period until said second detection sensor also detects the presence of the hydrocarbon and generates a second detection signal which is also transmitted to said communication means, said communications means includes a first switch including a time delay and a second switch operatively coupled to said first detection sensor and said second detection sensor to receive said first and second detection signal and to generate said data signal and a control signal In response thereto.

4. The oil spill detection system of claim 1 wherein said free floating tracking buoy comprises a lower ballast, an intermediate float chamber and an upper support structure to operatively support a radar reflector and a beacon and to operatively house a power source such as a storage battery electrically connected to the beacon by a conductor to selectively power the beacon when said free floating tracking buoy is deployed.

5. The oil spill detection system of claim 4 wherein said upper support structure is configured to operatively support a plurality of solar cells thereon.

6. The oil spill detection system of claim 5 wherein said upper support structure further supports a radar reflector thereon.

7. The oil spill detection of claim 4 wherein said upper support structure further supports a marine lantern thereon.

8. The oil spill detection system of claim 1 wherein said tracking buoy retainer device comprises an offset member having a clamp including a first and second clamp element respectively movable between an open and closed position and an actuator coupled to said communications means.

9. The oil spill detection system of claim 1 wherein said deployable free floating tracking buoy comprises a bulbous floatation member to operatively house a detection sensor and to operatively house a communication means including a power source including at least one storage battery, said detection sensor including means to detect the presence of hydrocarbons and generate a detection signal transmitted to said communication means, said communication means includes circuitry to generate a data signal in response to said detection signal and to transmit said data signal to a remote satellite station.

10. The oil spill detection system of claim 9 further incldes a ballast attached to said bulbous floatation member.

11. The oil spill detection system of claim 1 wherein said communication means includes circuitry to communicate with a remote satellite station.

* * * * *